(12) United States Patent
Beccard et al.

(10) Patent No.: US 10,267,768 B2
(45) Date of Patent: Apr. 23, 2019

(54) DEVICE AND METHOD FOR DETERMINING THE CONCENTRATION OF A VAPOR BY MEANS OF AN OSCILLATING BODY SENSOR

(71) Applicant: AIXTRON SE, Herzogenrath (DE)

(72) Inventors: Birgit Irmgard Beccard, Aachen (DE); Claudia Cremer, Jülich (DE); Karl-Heinz Trimborn, Wegberg (DE); Michael Long, Herzogenrath-Kohlscheid (DE); Andy Eichler, Aachen (DE); Nael Al Ahmad, Düren (DE)

(73) Assignee: AIXTRON SE, Herzogenrath (DE)

( * ) Notice: Subject to any disclaimer, the term of this patent is extended or adjusted under 35 U.S.C. 154(b) by 28 days.

(21) Appl. No.: 15/121,190

(22) PCT Filed: Feb. 23, 2015

(86) PCT No.: PCT/EP2015/053703
§ 371 (c)(1),
(2) Date: Aug. 24, 2016

(87) PCT Pub. No.: WO2015/128279
PCT Pub. Date: Sep. 3, 2015

(65) Prior Publication Data
US 2017/0016859 A1    Jan. 19, 2017

(30) Foreign Application Priority Data

Feb. 26, 2014 (DE) .................. 10 2014 102 484

(51) Int. Cl.
*B05D 1/00* (2006.01)
*B05B 12/00* (2018.01)
(Continued)

(52) U.S. Cl.
CPC ......... *G01N 29/022* (2013.01); *B05B 12/004* (2013.01); *B05B 12/008* (2013.01);
(Continued)

(58) Field of Classification Search
CPC ............... G01N 29/022; G01N 29/036; G01N 2291/0256
(Continued)

(56) References Cited

U.S. PATENT DOCUMENTS 4,472,345 A * 9/1984 Tanji .................... G21D 3/14
                                                    376/211
5,289,715 A    3/1994 Staples et al.
(Continued)

FOREIGN PATENT DOCUMENTS

DE       102008036050 A1 * 2/2010  ............. G01F 1/704
DE    10 2011 051 260 A1   12/2012
(Continued)

OTHER PUBLICATIONS

International Search Report dated May 20, 2015, from European Patent Office, for PCT/EP2015/053703 (filed Feb. 23, 2015), 5 pages.
(Continued)

*Primary Examiner* — Justin Seo
*Assistant Examiner* — John M Royston
(74) *Attorney, Agent, or Firm* — Ascenda Law Group, PC

(57) ABSTRACT

A device and a method determines the concentration of a vapor in a volume, in particular for determining or controlling the mass flow of the vapor being conveyed through the volume by a carrier gas. The device comprises a sensor, which supplies a sensor signal that is dependent on the concentration or partial pressure of the vapor. The sensor has an oscillatory body that can be brought to oscillation, the oscillation frequency of which is influenced by a mass
(Continued)

accumulation formed on a surface of the oscillating body by the condensed vapor. The oscillating body has a temperature control unit, by means of which the oscillating body can be brought to a temperature below the condensation temperature of the vapor. An evaluation unit determines the concentration or the partial pressure of the vapor from the temporal change of the oscillator frequency.

14 Claims, 1 Drawing Sheet

(51) Int. Cl.
  *G01N 29/02* (2006.01)
  *G01N 29/32* (2006.01)
  *G01N 29/036* (2006.01)

(52) U.S. Cl.
  CPC .............. *B05D 1/60* (2013.01); *G01N 29/036* (2013.01); *G01N 29/326* (2013.01); *G01N 2291/0212* (2013.01); *G01N 2291/0215* (2013.01); *G01N 2291/0256* (2013.01); *G01N 2291/02809* (2013.01)

(58) Field of Classification Search
  USPC .................................. 73/24.01, 24.04, 24.06
  See application file for complete search history.

(56) References Cited

U.S. PATENT DOCUMENTS

| | | | | |
|---|---|---|---|---|
| 5,402,748 | A * | 4/1995 | Takai | ...................... C30B 25/02 117/84 |
| 6,125,687 | A | 10/2000 | McClelland et al. | |
| 6,295,861 | B1 | 10/2001 | Tom et al. | |
| 7,990,025 | B1 * | 8/2011 | Ferreiro | .................. H01L 23/04 257/678 |
| 8,215,171 | B1 | 7/2012 | Smith et al. | |
| 2004/0129057 | A1 * | 7/2004 | Bonne | ...................... G01N 1/24 73/25.03 |
| 2005/0063882 | A1 | 3/2005 | Centanni et al. | |
| 2006/0179918 | A1 | 8/2006 | Liu | |
| 2009/0071229 | A1 * | 3/2009 | Grimshaw | ........... G01N 29/036 73/23.31 |
| 2010/0192675 | A1 * | 8/2010 | Schlichte | ................ G01N 27/16 73/31.06 |
| 2010/0294020 | A1 * | 11/2010 | Masuda | ................ G01N 29/022 73/24.01 |
| 2011/0201778 | A1 * | 8/2011 | Stoessel | ................ C07D 401/04 528/399 |
| 2013/0031956 | A1 * | 2/2013 | Mecea | .................. G01N 29/024 73/24.01 |
| 2015/0315707 | A1 * | 11/2015 | Xue | ....................... C23C 16/505 427/534 |

FOREIGN PATENT DOCUMENTS

| | | |
|---|---|---|
| DE | 10 2011 051 261 A1 | 12/2012 |
| DE | 10 2011 051 931 A1 | 1/2013 |
| WO | 2010/130775 A1 | 11/2010 |

OTHER PUBLICATIONS

Written Opinion dated May 20, 2015, from European Patent Office, for PCT/EP2015/053703 (filed Feb. 23, 2015), 6 pages.
Interational Preliminary Report on Patentability dated Aug. 30, 2016, from the International Bureau of WIPO, International Patent Application No. PCT/EP2015/053703 (filed Feb. 23, 2015), 16 pages.
Reply to Invitation to File Search Results dated Jun. 7, 2017, for European Patent Application No. EP15707077.2, 2 pages.
Request for Entry into the European Phase dated Sep. 23, 2016, for European Patent Application No. EP15707077.2, 11 pages.
Written Opinion dated May 20, 2015, from the ISA/European Patent Office, for International Patent Application No. PCT/EP2015/053703 (filed Feb. 23, 2015), Translation, 8 pages.

* cited by examiner

DEVICE AND METHOD FOR DETERMINING THE CONCENTRATION OF A VAPOR BY MEANS OF AN OSCILLATING BODY SENSOR

RELATED APPLICATIONS

This application is a National Stage under 35 USC 371 of and claims priority to International Application No. PCT/EP2015/053703, filed 23 Feb. 2015, which claims the priority benefit of DE Application No. 10 2014 102 484.2, filed 26 Feb. 2014.

FIELD OF THE INVENTION

The invention relates to a device and to a method for determining the concentration of a vapor in a volume, in particular for determining or controlling the mass flow of the vapor being conveyed through the volume by a carrier gas, wherein the volume can be heated or respectively is heated by means of a heating unit to a temperature above the condensation temperature of the vapor, comprising a sensor, which supplies a sensor signal that is dependent on the concentration of the vapor.

BACKGROUND

DE 10 2011 051 931 A1 describes an OLED coating device. In a deposition reactor, a susceptor is situated, the surface of which is cooled and carries a substrate which is to be coated. A carrier gas-vapor mixture is fed into the process chamber from a gas inlet member which is heated to a temperature above the condensation temperature of a vapor. The vapor condenses on the surface of the substrate, wherein the quality of the layer depends on the one hand on the concentration (the partial pressure) of the vapor in the process chamber, but on the other hand also on the temperature of the substrate surface. In a method for separating OLED layers on a substrate, the maintaining of a temporally constant vapor flow rate into the process chamber is desired. The vapor is generated in a vapor generator by the application of heat on a solid or liquid starting material. The starting material can be brought as an aerosol into a vaporization volume. The vaporization volume is flowed through by a carrier gas, with which the vapor is brought into the process chamber. The carrier gas is fed via a mass flow controller into the pipeline system of the vaporization device. With a second sensor, a sensor signal is obtained, which is influenced by the concentration (the partial pressure) of the vapor.

From WO 2010/130775 A1, US 2006/0179918 A1 and U.S. Pat. No. 8,215,171 B1 so-called QCM sensors (quartz crystal microbalance) are known. These sensors are used in vacuum vaporization devices, so-called VTE systems (vacuum thermal evaporation). A QCM sensor consists of a quartz crystal, which is stimulated to oscillate in its resonance frequency. In the vaporization, for example the vaporization of objects with metals, for example gold, or else also in the vaporization of objects with non-metals, a certain amount of vapor condenses on a portion of the surface of the oscillating body formed by the quartz. In the prior art, the oscillating body is kept at a temperature of approximately 50° C. During the coating process, a condensate layer grows on the surface of the oscillating body. This additional mass detunes the oscillating body, so that the frequency changes temporally. This takes place according to the so-called SAUERBREY equation. In the known use of this QCM sensor, the coating process is terminated when this oscillation frequency has reached a predetermined final value.

After a specified number of coating processes, the sensor must either be exchanged or cleaned, so that its oscillating capability is maintained, because the layers which are deposited on the quartz crystal influence not only the frequency, but also the amplitude, because they act in a damping manner.

Due to the type of construction, commercially available QCM sensors can not be used at high temperatures lying substantially above 50° C.

SUMMARY OF THE INVENTION

The invention is based on the problem of providing, in a generic device or in a generic method, in particular a method for separating OLED layers, a sensor for determining the vapor concentration, the sensor signal of which is not influenced, or at most slightly influenced, by the carrier gas.

The problem is solved by the method indicated in the claims and the device indicated in the claims.

Firstly and essentially it is proposed that a QCM is used as a sensor, therefore a sensor which has an oscillating body which is able to be brought to oscillation, the oscillation frequency of which is influenced by a mass accumulation, in particular layer, formed on a surface of the oscillating body by the condensed vapor. The oscillator frequency depends on the one hand on the thickness and on the other hand on the quality, therefore the physical but also chemical characteristics of the layer. The sensor is arranged in the volume, through which the carrier gas stream transports the vapor. Through the temporal alteration rate of the resonance frequency of the oscillator formed by the oscillating body, a value can be derived for the vapor concentration (partial pressure) within the volume. The flow rate of the vapor can then be determined from the flow rate of the carrier gas fed into the volume in a controlled manner and flowing through the volume.

The invention relates, furthermore, to the use of such a sensor in a gas supply of an OVPD coating device, which has a deposition reactor in which a coolable susceptor is arranged for receiving one or more substrates which are to be coated. The invention therefore also relates to a device for vaporizing a liquid or solid starting material with a heatable vaporizer, into which an inlet stream of a carrier gas enters through an inlet opening, which flows through the vaporizer and exits as outlet stream from the vaporizer through an outlet opening together with a vapor generated by vaporizing of the starting material. In the direction of flow before the inlet opening a first sensor is arranged for determining a first value associated with the mass flow of the inlet stream. The invention relates to the further development of a second sensor for determining a second value dependent on the partial pressure of the vapor. A value corresponding to the partial pressure of the vapor transported in the outlet stream is obtained by a computing unit of an evaluation unit and/or of a controller by correlating the two values. According to the invention, the second value is obtained from the temporal change of the oscillation frequency of the QCM sensor. With a corresponding method for generating a vapor transported in a carrier gas, the mass flow of the vapor can then be determined, which is fed into a process chamber of an OVPD coating system. The sensor can therefore be used as component of a closed control circuit, because response times of 0.1 second or less are able to be realized with it. The sensor signal of the sensor is fed to a controller, which can control the vaporization rate or respectively the mass flow of the carrier gas. Through a variation of the vapor generation rate or of the carrier gas flow, the conveying rate of the vapor can be adjusted and kept constant with a high degree of accuracy. The volume in which the sensor is situated can be heated to temperatures greater than 200° C., in particular greater than 350° C. and to temperatures which reach 450° C. A sensor crystal of gallium orthophosphate ($GaPO_4$) proves to be optimal when the sensor temperatures are to lie greater than 160° C. and preferably also greater than 180° C. The growth rate by which the vapor condenses on the surface of the oscillating body and the physical layer characteristics depend on the condensation temperature. It is advantageous if the sensor temperature lies only slightly below the condensation temperature. The temperature within the volume lies distinctly higher than the condensation temperature of the vapor, but is less than the breakdown temperature at which the vapor can break down chemically. The temperature of the sensor surface can be kept at a temperature which lies approximately 50° lower than the condensation temperature of the vapor or than the gas temperature lying above the condensation temperature of the vapor in the volume. The growth rate of the layer on the surface of the oscillating body influences the change in frequency of the oscillating body. Any non-linear correlations are taken into consideration via a correction factor. The sensor is preferably arranged within the gas stream which transports the vapor. The sensor surface is therefore acted upon with a relatively high vapor concentration. The surface temperature of the sensor is adjusted so that as small a growth rate as possible occurs, so that the sensor can be operated over a longer time. It is particularly advantageous if the sensor is able to be heated to temperatures above the condensation temperature of the vapor. It is able to be heated in particular to the temperature of the gas volume which can lie in the range between 200 and 450° C. With a temperature which is increased in such a manner, the coating evaporates from the oscillating body surface again, so that the sensor can be cleaned in situ. Two sensors can be used. The two sensors are connected respectively with the controller and can be used alternately. The sensor used for the regulating or respectively determining of the vapor concentration in the volume is cooled by means of a temperature control unit. The temperature control unit can have a cooling fluid duct which is flowed through by a cooling fluid. The oscillating body can be arranged in a housing which has the said cooling ducts, wherein the cooling ducts are preferably arranged so that only the oscillating body and in particular only its surface which is exposed to the vapor is cooled. With the use of two sensors, the sensor which is not used for controlling is not cooled. Its active surface of the oscillating body is therefore at a temperature at which a coating of the active surface can evaporate. In a preferred embodiment, the sensor housing has a closure device, by which an opening, toward the rear of which the active surface of the oscillating body is situated, can be closed, so that the active surface is not exposed to the vapor. Through the cyclic cleaning of the sensor surface by heating the sensor to a temperature which lies above the condensation temperature, the service life can be increased by a factor of 100 compared to the service life of QCM sensors, as are used according to the prior art mentioned in the introduction. The sensor according to the invention can be used at total gas pressures in the range of 0.1 and 10 mbar. The working temperature of the sensor lies between 200 and 400° C. The vapor in the carrier gas can have a mass percentage of 0.1 to 10%. The mass concentration of the vapor within the measuring cell is determined by the alteration rate of the oscillation frequency of the oscillating body. DE 10 2011 051 931 A1, DE 10 2011 051 261 A1 and DE 10 2011 051 260 A1 named in the introduction describe methods and devices for controlling the vapor production rate by, on the one hand, variation of the delivery rate of the material to be vaporized and, on the other hand, by variation of the vaporization temperature. The features concerning in particular the controlling function and the controlling device of these three publications are included in full into the disclosure content of this application. A preferred controlling device for controlling the vapor production rate comprises, according to the invention, two control circuits. With a first control circuit, which has a high time constant, is therefore a "slow" controller, an average vapor production rate is kept to a predetermined average value. This takes place through the variation of the delivery rate of the material which is to be vaporized. The mean delivery rate of the material which is to be vaporized corresponds in the long term to the average vapor production rate. With a second control circuit, which has a low time constant compared to the first control circuit, is therefore a "quick" controller, temporary deviations of a current vapor production rate from a mean value are compensated. Temporary deviations can have, for example, a periodic nature, when a conveying device for conveying the material which is to be vaporized, therefore preferably a powder which is to be vaporized, has mechanical, rotationally driven drive- or respectively conveying means. Temporary interferences in the constancy of the delivery rate can, however, also be due to a non-homogeneity of the powder which is to be vaporized. These temporary changes are compensated by raising or respectively lowering the vaporization temperature, wherein with the first control circuit the delivery rate is set so that the vaporization temperature can be varied both upward and downward. The vaporization temperature is limited downward by the condensation temperature and upward by the breakdown temperature of the material which is to be vaporized. With the first control circuit, the delivery rate is set so that in the averaged time the vaporization temperature lies approximately in the middle between an upper limit temperature and a lower limit temperature.

BRIEF DESCRIPTION OF THE DRAWINGS

An example embodiment of the invention is explained below with the aid of enclosed drawings. There are shown.

DETAILED DESCRIPTION OF THE INVENTION

Figure 1:
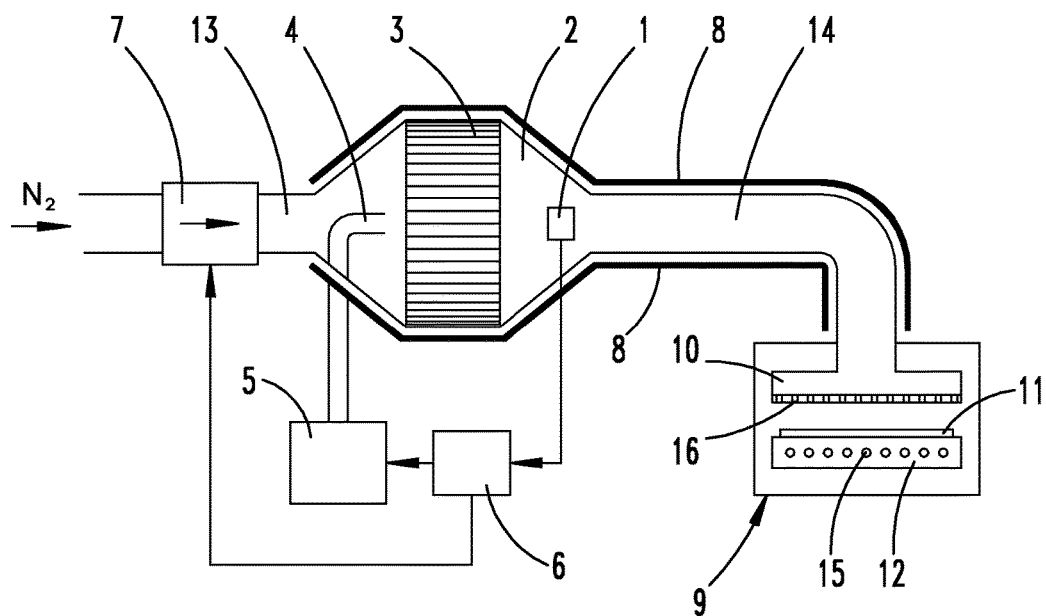
FIG. 1 diagrammatically the structure of an OLED coating device.

The coating device illustrated in FIG. 1 has a deposition reactor 9. This is a gas-tight container, in which a process chamber is situated, in which a total pressure of 0.1 to 100 mbar is able to be set. In particular, a controlled total pressure of 0.1 to 10 mbar is able to be set there. Within the deposition reactor 9 there is situated a susceptor 12, which has cooling ducts 15, through which a cooling fluid can flow, in order to keep the susceptor 12 at a defined deposition temperature. A substrate 11 which is to be coated lies on the upper side of the susceptor.

Above the susceptor 12 there is situated a shower-head-like gas inlet member 10, through which a vapor-carrier gas mixture can be introduced into the process chamber arranged between susceptor 12 and gas inlet member 10.

The gas inlet member 10 is kept at a temperature which lies above the condensation temperature of the vapor, so that a gaseous starting material is brought into the process chamber and the vapor can deposit itself on the substrate 11. The condensate of the vapor forms an OLED layer.

The gas inlet member 10 is fed by means of a vapor feeder line 14 with a carrier gas-vapor mixture, which is generated in a vapor generator 2,3,4. The vapor generator 2,3,4 and the vapor feeder line 14 are kept by means of a heating unit 8 at a temperature which lies above the condensation temperature of the vapor but below the breakdown temperature of the vapor.

By means of a mass flow controller 7, a defined flow of a carrier gas, for example nitrogen, is introduced into the vaporizer 2,3,4 through a feed line 13 forming an inlet opening.

In the example embodiment, the vaporizer has an injection chamber, into which an injector 4 opens, by which a solid body which is to be vaporized or a liquid which is to be vaporized is brought as an aerosol into the injection chamber. The aerosol arrives into a hot vaporization chamber 3, where it vaporizes. The liquid or the solid body is transported from a storage container via a conveying device. The injector 4 can be part of an aerosol generator 5, by which the solid body or the liquid is fed as an aerosol into the carrier gas stream. The conveying rate of the solid or liquid starting material which is to be vaporized or respectively the mass flow of the carrier gas is predetermined by a controller 6.

In the vaporization body 3, heat is supplied to the solid material which is to be vaporized or to the liquid which is to be vaporized, in particular the generated aerosol, so that the solid body or the liquid changes its aggregation state. The starting material leaves the vaporization body 3 as vapor transported in the carrier gas through a duct 14 forming an outlet opening. It reaches the volume 2, in which a sensor element 1 is situated, which is able to determine the mass concentration or respectively the partial pressure of the vapor within the volume 2. From the carrier gas mass flow set in the mass flow controller 7, the mass flow of the vapor through the duct 14 adjoining the volume 2, therefore the outlet duct, can be determined.

The controller 6 receives as input parameter either the sensor signal of the sensor 1 or else a measurement signal, obtained from the sensor signal 1 by measured value transformation, proportional to the mass flow of the vapor.

By variation of the conveying rate of the solid body which is to be vaporized, or of the liquid which is to be vaporized, or by variation of the vaporization temperature of the material which is to be vaporized and variation of the mass flow value fed in the mass flow controller 7, the mass flow of the vapor can be adjusted and kept temporally constant.

Figure 2:
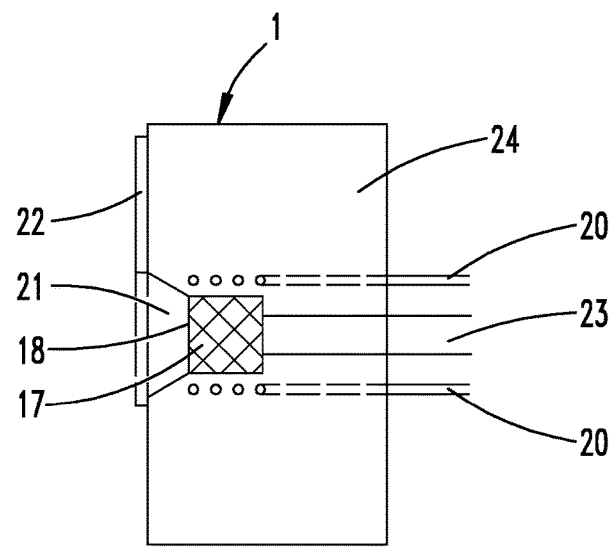
FIG. 2 diagrammatically the structure of a QCM sensor indicated in FIG. 1.

The sensor 1 illustrated in FIG. 2 has a housing 24. The housing 24 has an opening 21. The opening is able to be closed by means of a closure 22. The closure position is illustrated by dashed lines in FIG. 2. The base of the opening 21 is formed by an active surface 18 of a crystal of gallium orthophosphate or of a similar material. The crystal 17 is kept by means of a temperature control unit 20 at a temperature which is lower than the temperature of the volume 2. Whereas the temperature of the volume 2 lies above the condensation temperature of the vapor, therefore in particular above 350° C., the temperature of the crystal 17 and in particular the temperature of the active surface 18 lies at a temperature which is lower than the condensation temperature of the vapor, therefore for example at 300° C. This has the result that a layer, becoming thicker over time, is deposited on the surface 18. This layer is condensed vapor.

By means of an electrical excitation device, which is not illustrated, the crystal 17 forms an oscillating circuit. The resonance frequency of this oscillating circuit is determined by the physical characteristics of the crystal 17. The resonance frequency is, however, also influenced by the mass accumulation on the active surface 18. The condensed layer forms a mass accumulation on the active surface, which leads to a damping and to a detuning of the resonance frequency. For example, the resonance frequency can decrease with an increasing layer thickness. The frequency with which the crystal 17 oscillates is therefore a measurement for the thickness of the layer which is deposited on the active surface 18. Consequently, the alteration rate of the frequency is a measurement for the vapor concentration (the partial pressure) within the volume, because the deposition rate, therefore the growth rate of the layer deposited on the active surface 18 is dependent on the vapor concentration.

The growth rate of the layer deposited on the active surface 18 is, however, also dependent on the temperature of the crystal 17 or respectively the temperature of the active surface 18. In order to guarantee as long a time of use of the sensor as possible, provision is made that the temperature of the active surface lies only slightly below the condensation temperature. For example, the temperature of the active surface 18 can be 50° C. less than the condensation temperature of the vapor. Such a high temperature results not only in a small growth rate, but also the formation of a dense or respectively compact layer. The deposited layer forms with a minimal malposition concentration, therefore a densest packing of the molecules forming the layer. This results in a low damping of the oscillating behavior of the crystal 17. A smaller growth rate suppresses, furthermore, diffusion influences which the carrier gas has on the growth rate.

The vapor consists of aromatic hydrocarbons, which as a solid body have a higher elasticity than metal or other inorganic materials.

With the method according to the invention, by means of the previously described sensor 1 the mass concentration of a vaporized organic starting material in a carrier gas can be determined selectively. $N_2$ is used for example as carrier gas. This takes place at raised temperatures above 200° C. and at gas pressures in the range of 0.1 and 10 mbar. The proportion of the vapor in the vapor-carrier gas mixture can be 0.1 to 10%. The sensor 1 achieves a response time of less than 0.1 seconds. As part of a control circuit, a vapor feed rate can be kept temporally constant with the sensor 1.

As the sensor according to the invention can be cleaned automatically and in situ by heating the active surface 18 to a temperature above the condensation temperature, a preferred variant of the invention has two or more such sensors 1, which can be used optionally for controlling. The sensor which is used for controlling is cooled to a temperature below the condensation temperature of the vapor via the feed line/discharge line 20 with a cooling fluid, which is fed into the cooling ducts 15 of the temperature control unit. The sensor frequency is supplied to the controller 6 via electric lines 23. The opening 21 is opened.

A sensor 1 which is not used for controlling is not cooled. Its active surface 18 has a temperature which lies above the condensation temperature of the vapor, so that a layer which is formed there can vaporize or so that no layer grows there. The opening 21 can, however, also be closed with the closure 22.

The controller 6 provides two variables. With a first variable, the delivery rate of a material which is to be vaporized, in particular of a powder which is to be vaporized, is set. For example, this can take place by controlling the rotation speed of a worm conveyor, by which a powder is conveyed to an aerosol generator, by which it is brought into a gas stream which is directed to vaporizer surfaces. With a second variable, the temperature of the vaporizer surfaces is set. Certain amounts of the powder which is to be vaporized can adhere to the vaporization surfaces and thus form a reservoir. By means of this reservoir, through variation of the vaporization temperature, the vapor production rate can be varied in the short term. The long-term variation of the vapor production rate takes place by controlling the conveying rate with which the material which is to be vaporized is brought into the vaporizer.

The controller 6 therefore comprises two control circuits. With the first control circuit, which has a high time constant, the delivery rate of the material which is to be vaporized is controlled. The delivery rate is set so that an average vapor production rate is kept to a predetermined nominal value. With the second control circuit, the vaporization temperature is altered. The second control circuit has a low time constant compared to the time constant of the first control circuit. With this second control circuit, temporary deviations of the vapor production rate can be reacted to by altering the vaporization temperature. For example, by lowering the vaporization temperature, the vaporization capacity can be reduced. Hereby, a storage mass can collect in the vaporizer. By raising the vaporization temperature, this storage mass can be vaporized, in order to react to a temporary lowering of the delivery rate.

A control method which is used here, or respectively a control device which is to be used, are described by DE 10 2011 051 261 A1, DE 10 2011 051 260 A1 and DE 10 2011 051 931 A1, which belong to the subject of the disclosure of this application.

The above statements serve to explain the inventions encompassed by the application as a whole, which further develop the prior art at least through the following feature combinations respectively independently, namely:

A device, which is characterized in that the sensor 1 has an oscillating body 17 able to be brought to oscillation, the oscillation frequency of which is influenced by a mass accumulation formed on a surface 18 of the oscillating body 17 by the condensed vapor, wherein the oscillating body 17 has a temperature control unit 20, by which it is able to be brought to a temperature below the condensation temperature of the vapor, wherein an evaluation unit determines the concentration or respectively the partial pressure from the temporal change of the oscillator frequency.

A method, which is characterized in that the sensor 1 has an oscillating oscillation body 17, the oscillation frequency of which is influenced by a mass accumulation formed on a surface 18 of the oscillating body 17 by the condensed vapor, wherein the oscillating body 17 is brought by means of a temperature control unit 20 to a temperature below the condensation temperature of the vapor and the concentration or respectively the partial pressure is determined from the temporal change of the oscillator frequency.

A device or a method which are characterized in that the temperature control unit 20 is a cooling unit, by which the oscillating body 17 is cooled.

A device or a method, which are characterized in that the oscillating body 17 is a crystal of gallium orthophosphate ($GaPO_4$).

A device or a method, which are characterized in that by means of a feed-in device 13 a carrier gas is fed into a vaporizer 2,3,4, into which a liquid or a solid body is brought into a gaseous state by application of heat, wherein the flow rate of the carrier gas and/or the vapor production rate of the vaporizer 2,3,4 is able to be changed by a controller 6, which together with the sensor 1 forms a closed control circuit.

A device or a method, which are characterized in that the controller 6 has two control circuits for controlling the vapor production rate: A first control circuit, having a high time constant, by which an average vapor production rate is controlled to a predetermined average value by variation of the delivery rate of the material which is to be vaporized, and a second control circuit having a low time constant, by which temporary deviations of the current vapor production rate from the average value are compensated by changing the vaporization temperature.

A device or a method, which are characterized in that the sensor 1, the vaporizer 2,3,4 are parts of a gas supply of an OVPD coating device, which has a deposition reactor 9, into which a coolable susceptor 12 is arranged for receiving one or more substrates 11 which are to be coated, wherein through a feed line 13 an inlet gas stream of a carrier gas enters into the vaporizer 2,3,4, which flows through the vaporizer 2,3,4 and together with the vapor generated in the vaporizer 2,3,4 by vaporizing a starting material, exits as outlet stream from the vaporizer 2,3,4 through a feeder line 14, wherein the mass flow of the inlet stream is determined by a sensor element 7 arranged in front of the inlet opening and with the sensor 1 a value dependent on the partial pressure of the vapor, wherein by means of a computing unit, by correlating the two values, a value is obtained corresponding to the mass flow of the vapor which is transported in the outlet stream.

A device or a method, which are characterized in that the sensor 1 is able to be heated to temperatures up to 450° C.

A device or a method, which are characterized in that the surface 18 is able to be closed by means of a closure 22.

A device or a method, which are characterized in that two sensors 1 of identical construction are used, wherein respectively one sensor 1 is kept at a temperature below the condensation temperature of the vapor and in particular below the temperature of the volume 2, and the respectively other sensor 1 is kept at a temperature above the condensation temperature and in particular at the temperature of the volume 2.

A device or a method, which is characterized in that the sensor 1 is kept at a temperature of greater than 160° C., preferably greater than 180° C. and particularly preferably at a temperature of 50° C. below the temperature of the volume 2, and/or that the temperature of the volume 2 is greater than 200° C., greater than 350° C. and in particular less than 450° C.

A device or a method, which are characterized in that the sensor 1 is heated, for cleaning, to a temperature above the condensation temperature of the vapor, so that the condensate formed on the sensor surface evaporates.

A device or a method, which are characterized in that the total pressure within the volume 2 lies in the range between 0.1 and 10 mbar, and/or that the mass concentration of the vapor in the carrier gas lies in the range between 0.1 and 10%.

All disclosed features are (in themselves, but also in combination with one another) essential to the invention. The disclosure content of the associated/enclosed priority documents (copy of the prior application) is herewith also included in full into the disclosure of the application, also for the purpose of including features of these documents into claims of the present application. The subclaims characterize with their features independent inventive further developments of the prior art, in particular in order to carry out divisional applications on the basis of these claims.

LIST OF REFERENCE NUMBERS 1 sensor
2 volume
3 vaporization body
4 injector
5 aerosol generator
6 controller
7 mass flow regulator, controller
8 heating unit
9 deposition reactor
10 gas inlet member
11 substrate
12 susceptor
13 feed line
14 vapor feeder line
15 cooling duct
16 gas outlet opening
17 crystal
18 surface
20 feed line/discharge line, temperature control unit
21 opening
22 closure
23 line
24 housing

What is claimed is:

1. A device, comprising:
a volume (2) for conveying a vapor by means of a carrier gas;
a heating unit (8) for heating said volume (2) to a first temperature above a condensation temperature of the vapor;
a sensor (1), situated in the volume (2), which supplies a sensor signal that is dependent on a concentration or a partial pressure of the vapor, the sensor (1) including an oscillating body (17) that is brought to oscillation, an oscillation frequency of which is influenced by a mass accumulation formed on a surface (18) of the oscillating body (17) by a condensation of the vapor, wherein the oscillating body (17) has a temperature control unit (20), by means of which the oscillating body is brought to a second temperature below the condensation temperature of the vapor;
a controller (6) configured to determine the concentration or the partial pressure of the vapor from a temporal change of the oscillation frequency, and control a mass flow of the vapor based on the determined concentration or the partial pressure of the vapor; and
a feed-in device (13) with a mass flow controller (7) for setting a mass flow of the carrier gas that is fed into a vaporizer (2, 3, 4), in which a liquid or a solid body is brought into a gaseous state by an application of heat,
wherein the mass flow of the carrier gas and/or a vapor production rate of the vaporizer (2, 3, 4) or a vaporization temperature is changed by the controller (6), which together with the sensor (1) forms a closed control circuit in which the sensor signal from the sensor (1) is used by the controller (6) to control the mass flow of the carrier gas and/or the vapor production rate of the vaporizer so as to keep the mass flow of the vapor temporally constant.

2. The device according to claim 1, wherein the temperature control unit (20) is a cooling unit, by which the oscillating body (17) is cooled.

3. The device according to claim 1, wherein the oscillating body (17) is a crystal of gallium orthophosphate ($GaPO_4$).

4. The device according to claim 1, wherein the controller (6) has a first and second control circuit for controlling the vapor production rate, the first control circuit having a high time constant, by which an average vapor production rate is controlled to a predetermined average value by variation of a delivery rate of a material which is to be vaporized, and the second control circuit having a low time constant, by which temporary deviations of the vapor production rate from the predetermined average value are compensated by changing the vaporization temperature.

5. The device according to claim 1, wherein the sensor (1), and the vaporizer (2, 3, 4) are parts of a gas supply of an organic vapor phase deposition (OVPD) coating device, which has a deposition reactor (9), in which a coolable susceptor (12) is arranged for receiving one or more substrates (11) which are to be coated, wherein through the feed-in device (13) an inlet gas stream of the carrier gas enters into the vaporizer (2, 3, 4), which flows through the vaporizer (2, 3, 4) and together with the vapor generated in the vaporizer (2, 3, 4) by vaporizing a starting material, exits as an outlet stream from the vaporizer (2, 3, 4) through a feeder line (14), wherein a first value corresponding to a mass flow of the inlet gas stream is determined by the mass flow controller (7) arranged in front of an inlet opening and a second value dependent on the partial pressure of the vapor is determined by the sensor (1), wherein by means of a computing unit, by correlating the first and second values, a third value is obtained corresponding to the mass flow of the vapor which is transported in the outlet stream.

6. The device according to claim 1, wherein the sensor (1) and the volume (2) are able to be heated to temperatures in a range between 200° C. and 450° C.

7. The device according to claim 1, further comprising a closure (22) which encloses the surface (18) of the oscillating body (17).

8. A method, comprising:
conveying a vapor by means of a carrier gas into a volume (2);
heating the volume (2) by means of a heating unit (8) to a first temperature above a condensation temperature of the vapor;
supplying a sensor signal from a first sensor (1), situated in the volume (2), the first sensor signal dependent on a concentration or a partial pressure of the vapor, wherein the first sensor (1) has an oscillating body (17), an oscillation frequency of which is influenced by a mass accumulation formed on a surface (18) of the oscillating body (17) by a condensation of the vapor;
controlling by a temperature control unit (20) a temperature of the oscillating body (17) of the first sensor to a second temperature below the condensation temperature of the vapor;
while controlling the temperature of the oscillating body (17) of the first sensor to the second temperature below the condensation temperature of the vapor, controlling the temperature of a second sensor, situated in the volume (2), to a third temperature above the condensation temperature of the vapor, wherein the first sensor and second sensor have identical construction;
determining by a controller (6) the concentration or the partial pressure of the vapor from a temporal change of the oscillation frequency of the first sensor (1); and
controlling by the controller (6) a mass flow of the vapor based on the determined concentration or the partial pressure of the vapor.

9. The method according to claim 8, wherein the first sensor (1) is maintained at a temperature greater than 160° C.

10. The method according to claim 9, wherein the temperature of the volume (2) is greater than 200° C.

11. The method according to claim 8, wherein, during a cleaning step, the first sensor (1) is heated, to a fourth temperature above the condensation temperature of the vapor, so that the mass accumulation formed on the surface (18) of the oscillating body (17) evaporates.

12. The method according to claim 8, wherein a total pressure within the volume (2) lies in a range between 0.1 and 10 mbar, and/or the concentration of the vapor lies in a range between 0.1 and 10%.

13. The method of claim 8, wherein a mass flow of carrier gas is fed via a feed-in device (13) into the volume (2), in which the vapor is created.

14. A device, comprising:
a volume (2) for conveying a vapor by means of a carrier gas;
a heating unit (8) for heating said volume (2) to a first temperature above a condensation temperature of the vapor;
a first sensor and a second sensor of identical construction, the first and second sensor situated in the volume (2), the first sensor supplying a sensor signal that is dependent on a concentration or a partial pressure of the vapor, the first sensor including an oscillating body (17) that is brought to oscillation, an oscillation frequency of which is influenced by a mass accumulation formed on a surface (18) of the oscillating body (17) by a condensation of the vapor, wherein the oscillating body (17) has a temperature control unit (20), by means of which the oscillating body of the first sensor is maintained at a second temperature below the condensation temperature of the vapor, wherein while the oscillating body of the first sensor (1) is maintained at the second temperature below the condensation temperature of the vapor, the second sensor (1) is maintained at a third temperature above the condensation temperature; and
a controller (6) configured to determine the concentration or the partial pressure of the vapor from a temporal change of the oscillation frequency of the first sensor (1), and control a mass flow of the vapor based on the determined concentration or the partial pressure of the vapor.

* * * * *